United States Patent [19]

Wu

[11] Patent Number: 6,114,535
[45] Date of Patent: Sep. 5, 2000

[54] PROCESS AND INTERMEDIATES FOR THE MANUFACTURE OF PYRIDINE-2,3-DICARBOXYLATE COMPOUNDS

[75] Inventor: Wen-Xue Wu, North Brunswick, N.J.

[73] Assignee: American Cyanamid Company, Madison, N.J.

[21] Appl. No.: 09/479,294

[22] Filed: Jan. 6, 2000

Related U.S. Application Data

[62] Division of application No. 09/333,350, Jun. 15, 1999, which is a division of application No. 09/097,871, Jun. 15, 1989, Pat. No. 5,925,764.
[60] Provisional application No. 60/089,389, Jun. 15, 1998.

[51] Int. Cl.$^7$ .................................................. C07D 401/14
[52] U.S. Cl. ........................................................ 546/274.1
[58] Field of Search ........................................... 546/274.1

[56] References Cited

U.S. PATENT DOCUMENTS

| | | | |
|---|---|---|---|
| 4,723,011 | 2/1988 | Doehner, Jr. | 546/250 |
| 4,948,896 | 8/1990 | Nagao | 546/250 |
| 4,973,695 | 11/1990 | Yamashita et al. | 546/250 |
| 5,008,392 | 4/1991 | Meier et al. | 546/250 |
| 5,047,542 | 9/1991 | Gupton et al. | 546/250 |
| 5,101,067 | 3/1992 | Meier et al. | 560/171 |
| 5,175,300 | 12/1992 | Yamashita et al. | 546/250 |
| 5,252,739 | 10/1993 | Yamashita et al. | 546/250 |

FOREIGN PATENT DOCUMENTS

| | | |
|---|---|---|
| 0461401 | of 0000 | European Pat. Off. . |
| 295803 | of 0000 | Japan . |
| 295804 | of 0000 | Japan . |

Primary Examiner—John Kight
Assistant Examiner—Binta Robinson
Attorney, Agent, or Firm—John W. Hogan, Jr.

[57] ABSTRACT

The present invention provides a process to prepare a pyridine-2,3-dicarboxylate derivative via the reaction of a dialkyl alkoxy(or alkylthio)oxalacetate with an appropriately substituted acrolein compound in the presence of an ammonia source and a solvent.

The present invention also provides useful intermediate compounds of formula IV.

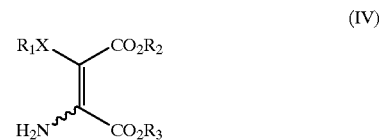

(IV)

1 Claim, No Drawings

PROCESS AND INTERMEDIATES FOR THE MANUFACTURE OF PYRIDINE-2,3-DICARBOXYLATE COMPOUNDS

This is a divisional of copending application(s) Ser. No. 09/333,350 now allowed filed on Jun. 15, 1999 which is a divisional of U.S. Ser. No. 09/097,871 filed Jun. 15, 1998 (now U.S. Pat. No. 5,925,764) and claims priority to U.S. application Ser. No. 60/089,389 filed Jun. 15, 1998—has been inserted after the phrase—now U.S. Pat. No. 5,925, 764)—and amended to reflect the provisional application the entire disclosure of each being hereby incorporated by reference.

BACKGROUND OF THE INVENTION

Pyridine-2,3-dicarboxylate derivatives are useful intermediates for the preparation of herbicidal 2-(2-imidazolin-2-yl)nicotinic acids, esters and salts such as those described in U.S. Pat. No. 5,334,576 and U.S. Pat. No. 4,798,619. Literature methods for preparing substituted pyridine-2,3-dicarboxylates include degradative techniques which require hazardous oxidative methods such as nitric acid oxidation or base peroxide oxidation of the 2,3-dialkyl or quinolinic precursors. Conventional de novo syntheses of pyridine-2, 3-dicarboxylates which employ oxalacetate diesters, or their metal salts, such as those described in U.S. Pat. No. 5,047, 542 and JP 01125768A generally give products in low yield and low purity. The use of halogenated oxalacetate diesters to prepare pyridine-2,3-dicarboylate derivatives, although effective, require the formation of unstable $\alpha$-halo-$\beta$-keto esters such as diethyl chlorooxalacetate, which are known to thermally decompose, releasing HCl gas and creating potentially hazardous and toxic conditions.

Surprisingly, it has now been found that pyridine-2,3-dicarboxyalte derivatives may be effectively and economically prepared using amino alkoxy(or alkylthio)oxalacetate diester compounds, either as starting materials or as in situ intermediates.

Therefore, it is an object of this invention to provide a safe, effective, economic and environmentally compatible process to manufacture pyridine-2,3-dicarboxylate derivatives.

It is another object of this invention to provide a readily available, easily accessible source of starting materials, useful for said process.

It is a feature of the process of the invention that the major side products are alcohols and thiols which may be readily recovered by distillation or extraction.

It is another feature of the process of the invention that the recovered alcohols and thiols may be recycled to produce additional starting material, resulting in minimum waste.

It is an advantage that the compounds of the invention are thermally and chemically stable over a convenient range of conditions and thus require no special handling and present no particular risk to the handlers or the environment.

Further features and objects of the invention will become apparent in the detailed description thereof set forth hereinbelow.

SUMMARY OF THE INVENTION

The present invention provides a process for the manufacture of a compound of formula I

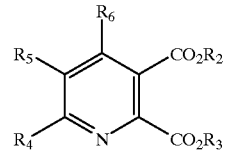

(I)

wherein $R_4$ and $R_6$ are each independently H, $C_1$–$C_6$ alkyl, $C_1$–$C_6$alkenyl, phenyl or substituted phenyl;

$R_5$ is H; halogen; $C_1$–$C_6$alkyl optionally substituted with one or more $C_1$–$C_4$alkoxy groups; $C_1$–$C_6$alkenyl; phenyl or substituted phenyl; and $R_2$ and $R_3$ are each independently $C_1$–$C_6$alkyl, phenyl or substituted phenyl;

which comprises reacting a compound of formula II or an alkali metal salt thereof

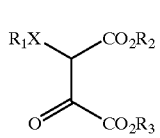

(II)

wherein X is O or S; $R_1$ is $C_1$–$C_6$alkyl, phenyl or substituted phenyl; and $R_2$ and $R_3$ are as described for formula I; with at least one molar equivalent of a compound of formula III

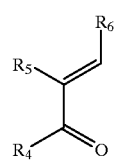

(III)

wherein $R_4$, $R_5$ and $R_6$ are as described for formula I; and an ammonia source in the presence of a solvent optionally at an elevated temperature.

The present invention also provides a process for the preparation of a compound of formula I

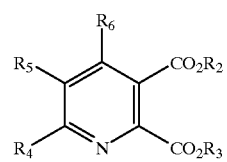

(I)

wherein $R_4$ and $R_6$ are each independently H, $C_1$–$C_6$alkyl, $C_1$–$C_6$alkenyl, phenyl or substituted phenyl;

$R_5$ is H, halogen, $C_1$–$C_6$alkyl optionally substituted with one or more $C_1$–$C_4$alkoxy groups, $C_1$–$C_6$alkenyl, phenyl or substituted phenyl; and $R_2$ and $R_3$ are each independently $C_1$–$C_6$alkyl, phenyl or substituted phenyl which comprises reacting a compound of formula IV

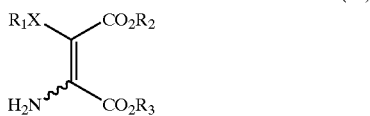
(IV)

wherein X is O or S; $R_1$ is $C_1$–$C_6$alkyl, phenyl or substituted phenyl; and $R_2$ and $R_3$ are as described for formula I with at least one molar equivalent of a compound of formula III or an alkali metal salt thereof

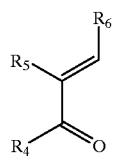
(III)

wherein $R_4$, $R_5$ and $R_6$ are as described for formula I in the presence of a solvent optionally at an elevated temperature.

The present invention further provides intermediate compounds of formula IV

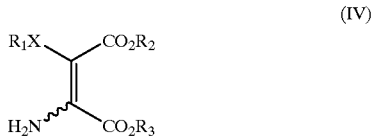
(IV)

wherein X is O or S; $R_1$ is $C_1$–$C_6$alkyl, phenyl or substituted phenyl; and $R_2$ and $R_3$ are each independently $C_1$–$C_6$alkyl, phenyl or substituted phenyl.

The pyridine-2,3-dicarboxylate compounds of formula I are useful as intermediates in the manufacture of highly potent, environmentally benign, imidazoline herbicidal agents of formula V

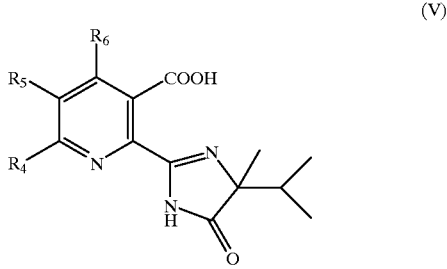
(V)

wherein $R_4$ and $R_6$ are each independently H, $C_1$–$C_6$ alkyl, $C_1$–$C_6$alkenyl, phenyl or substituted phenyl; and $R_5$ is H; halogen; $C_1$–$C_6$alkyl optionally substituted with one or more $C_1$–$C_4$alkoxy groups; $C_1$–$C_6$alkenyl; phenyl or substituted phenyl.

DETAILED DESCRIPTION OF THE INVENTION

Heretofore, de novo syntheses of pyridine-2,3-dicarboxylate derivates have been plagued by low yield and low purity products or the use of unstable halogenated oxalacetate intermediates. Now, it has been discovered that formula I pyridine-2,3-dicarboxylate derivatives may be effectively and efficiently prepared by the reaction of an amino alkoxy(or alkylthio)maleate or fumarate of formula IV with at least one molar equivalent of an α,β-unsaturated ketone of formula III in the presence of a solvent optionally at an elevated temperature. The process of the invention is illustrated in flow diagram I wherein X, $R_1$, $R_2$, $R_3$, $R_4$, $R_5$ and $R_6$ are as described hereinabove.

Flow Diagram I

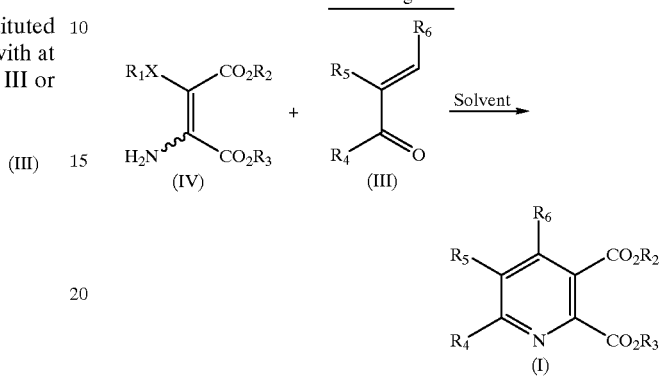

The term substituted phenyl as used in the specification and claims designates a phenyl ring substituted with one or more substituents which may be the same or different including halogen, $NO_2$, CN, OH, $C_1$–$C_4$alkyl, $C_1$–$C_4$haloalkyl, $C_1$–$C_4$alkoxy, $C_1$–$C_4$alkylthio, $C_1$–$C_4$haloalkoxy, $C_1$–$C_4$alkylamino, di($C_1$–$C_4$) alkylamino), and/or $C_1$–$C_4$alkylsulfonyl. Halogen designates Cl, Br, I or F. Haloalkyl designates an alkyl group substituted with one or more halogens which may be the same or different, and haloalkoxy designates an alkoxy group substituted with one or more halogens which may be the same or different.

Solvents suitable for use in the inventive process may be any organic solvent which will partially or completely solubilize the reactants and which will not participate in the reaction. Examples of organic solvents which may be used include alkanols, chlorohydrocarbons, hydrocarbons, aromatic hydrocarbons, ethers, carboxylic acids and esters, carboxylic acid nitriles, carboxamides, and the like, or mixtures thereof. Preferable solvents are alkanols such as methanol, ethanol, propanol, isopropanol, butanol, and the like, preferably ethanol; and aromatic hydrocarbons such as benzene, toluene, xylene, naphthalene, and the like, preferably toluene, or mixtures of alkanols and aromatic hydrocarbons, preferably mixtures of ethanol and toluene.

In general, the reaction temperature is inversely related to reaction time, i.e., increased temperatures lead to decreased reaction time. However, excessively high reaction temperatures may cause undesirable side reactions and decomposition. In general, suitable reaction temperatures may range from 25° C.–185° C.; preferably the reaction temperature is above 40° C.; especially preferred is a range from 80° C. to 100° C.

Thus, in accordance with the process of the invention, pyridine-2,3-dicarboxylates containing substituents in the 4, 5 and 6 positions may conveniently be prepared by admixing essentially equimolar amounts of a formula IV amino alkoxy (or alkylthio)diester and an α,β-unsaturated ketone of formula III in the presence of a suitable solvent at a temperature range of ambient temperatures to the boiling point of the solvent, preferably at reflux temperatures, until the reaction is complete. The formula I product thus formed may be isolated by conventional chemical process techniques such as extraction, filtration, distillation, chromatography, and the like. Alternatively, the formula I pyridine-2,3-dicarboxylate may be carried forth in a process stream without further purification/isolation steps.

The present invention also provides compounds of formula IV

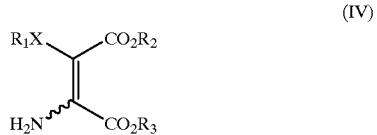

wherein X is O or S;

R$_1$ is C$_1$–C$_6$alkyl, phenyl or substituted phenyl; and

R$_2$ and R$_3$ are each independently C$_1$–C$_6$alkyl, phenyl or substituted phenyl.

The compounds of the invention may exist as the cis and trans isomers, IVa and IVb, respectively.

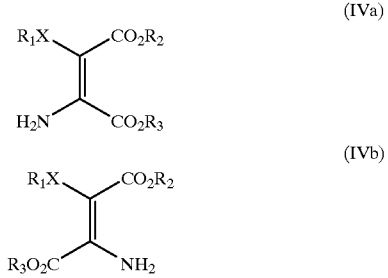

In the specification and claims, compounds of formula IV, as illustrated hereinabove designate the cis isomer (IVa), the trans isomer (IVb), or mixtures thereof. Preferred compounds of formula IV are those compound wherein X is O and R$_1$ is methyl, ethyl or phenyl.

The compounds of the invention are readily prepared by reacting an alkoxy(or alkylthio)oxalacetate of formula II with an ammonia source in the presence of a solvent. Advantageously, the formula IV compound of the invention may be formed in situ and, without further isolation steps, be reacted with a formula III α,β-unsaturated ketone to form the desired formula I pyridine-2,3-dicarboxylate product. This further process of the invention is shown in flow diagram II.

Ammonia sources suitable for use in the process of the invention include, but are not limited to, gaseous ammonia or ammonium salts such as ammonium acetate, ammonium bicarbonate, ammonium sulfamate, ammonium formate and the like. Preferable ammonium salts are ammonium acetate, ammonium sulfamate or ammonium bicarbonate.

Solvents and temperatures suitable for use in this process of the invention are the same as those described hereinabove for flow diagram I.

The formula II oxalacetates may also be employed in the process of the invention as their alkali metal salts, as shown hereinbelow wherein M is an alkali metal such as sodium or postassium.

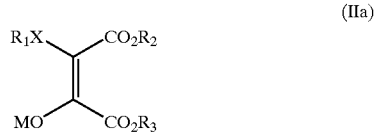

In the specification and claims, compounds of formula II designate the formula II free oxalacetates and the formula IIa alkali metal salt thereof.

Preferred compounds of formula II are those compounds wherein X is O and R$_1$ is methyl, ethyl or phenyl.

Preferred compounds of formula III are those compounds wherein R$_4$ and R$_6$ are H and R$_5$ is H or C$_1$–C$_4$alkyl optionally substituted with one C$_1$–C$_4$alkoxy group. More preferred formula II compounds are those compounds wherein R$_4$ and R$_6$ are H and R$_5$ is H, methyl, ethyl or methoxymethyl.

Thus, in accordance with a further process of the invention, pyridine-2,3-dicarboxylates containing substituents in the 4, 5 and 6 position may be conveniently prepared by admixing essentially equimolar amounts of an alkoxy (or alkylthio)oxalacetate of formula II or an alkali metal salt thereof, an α,β-unsaturated ketone of formula III, and an ammonia source in the presence of a suitable solvent at a temperature range of ambient temperatures to the boiling point of the solvent, preferably at reflux temperatures, until the reaction is essentially complete. The formula I product thus formed may be isolated by conventional procedures such as extraction, filtration, chromatography or the like. Alternatively, the formula I pyridine-2,3-dicarboxylate may be carried forth in a process stream, as is, without additional purification/isolation steps.

Formula I pyridine-2,3-dicarboxylates are useful intermediates for the preparation of herbicidal 2-(2-imidazolin-2-

FLOW DIAGRAM II

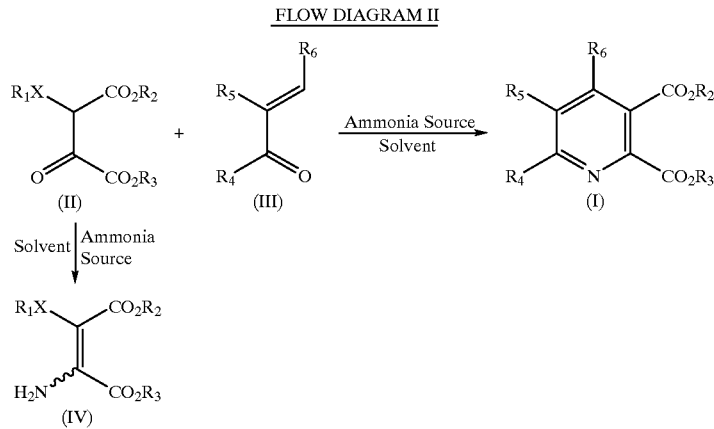

yl)nicotinic acids, esters and salts of formula V. For example, the formula I pyridine-2,3-dicarboxylate compound as formed in flow diagram I or flow diagram II may be reacted with a suitable aminocarboxamide compound of formula VI in the presence of an inert solvent and a strong base to give the formula V imidazolinone compound as shown in flow diagram III.

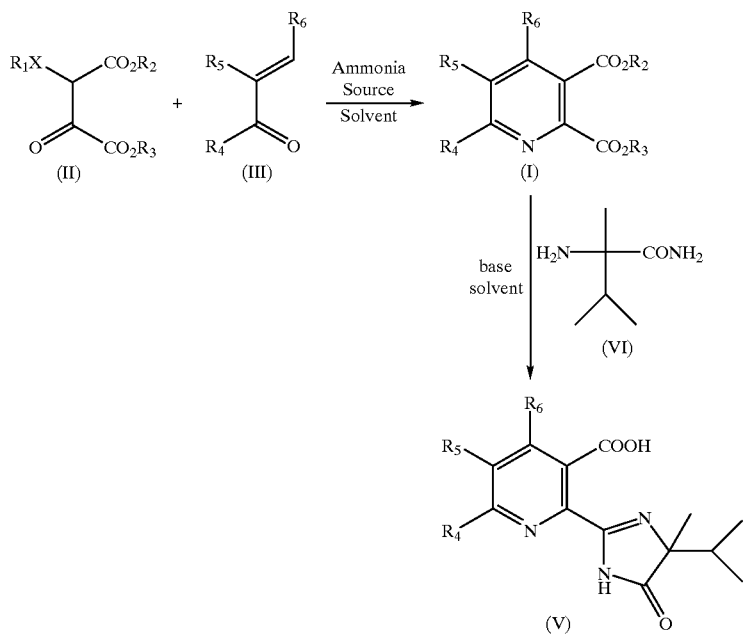

FLOW DIAGRAM III

Alternatively, the formula I diester as produced by the processes of the invention as illustrated in flow diagrams I and II may be hydrolyzed to the corresponding diacid, and employed in any of the process routes described in the patent literature for preparing the formula V imidazolinones, such as those described in U.S. Pat. No. 4,798,619.

In order to facilitate a further understanding of the invention, the following examples are presented primarily for the purpose of illustrating certain more specific details thereof and the invention is not to be deemed limited thereby.

The terms $^{13}$CNMR and $^{1}$HNMR designate Carbon 13 and proton nuclear magnetic resonance, respectively. The terms HRGC and HPLC designate high resolution gas chromatography and high performance liquid chromatography respectively. All parts are parts by weight, unless otherwise specified.

EXAMPLE 1

Preparation of Ethyl Ethoxyacetate

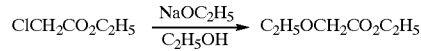

A solution of ethyl chloracetate (100 g, 99% pure, 0.81 mol) in ethanol is treated with ethanolic sodium ethoxide (282.9 g, 20.6% solution, 0.86 mole $NaOC_2H_5$) over a 1 hr period at 20° C.–30° C., heated at 40° C.–45° C. for 0.5 hr, cooled to room temperature, treated with diatomaceous earth, stirred for 0.25 hr and filtered. The filtercake is washed with ethanol. The combined filtrates are distilled to obtain the title product as a colorless liquid 75.78 g, 98.8% pure (71% yield), bp 87° C.–88° C./59 mmHg, identified by $^{13}$CNMR, $^{1}$HNMR and mass spectral analyses.

EXAMPLE 2

Preparation of Diethyl Ethoxyoxalacetate (stepwise addition method)

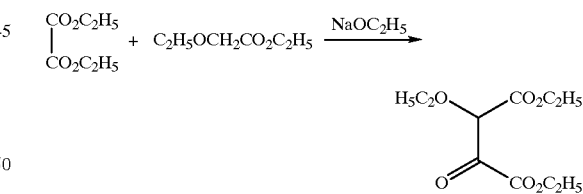

A stirred mixture of molten sodium metal (24.15 g, 1.05 mol) in toluene is treated with ethanol (55.2 g, 1.2 mol) over a 1 hr period at 100° C.–110° C., heated at reflux temperatures for 0.5 hr, cooled to 30° C., treated with diethyl oxalate (160.6 g, 1.1 mol) over a 10 min period at 30° C.–45° C., treated with ethyl ethoxyacetate (132 g, 98%, 0.98 mol) over an 0.5 hr period at 45° C.–50° C., heated at 55° C.–60° C. for 1.5 hr and poured into 328 g of 14% HCl with cooling. The resultant mixture is separated. The title product is obtained in the organic phase as a 40.9% solution, identified by HRGC analysis, total yield is 204.2 g (90% yield).

EXAMPLE 3

Preparation of Diethyl Ethoxyoxalacetate (Pre-blended method)

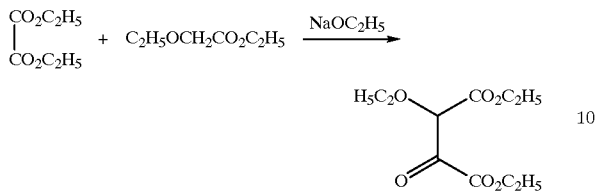

A stirred mixture of molten sodium metal (24.15 g, 1.05 mol) in toluene is treated with ethanol (55.2 g, 1.2 mol) over a 1 hr period at 100° C.–110° C., heated at reflux temperatures for 0.5 hr, cooled to 45° C., treated with a mixture of diethyl oxalate (160.6 g, 1.1 mol) and ethyl ethoxyacetate (132 g, 98%, 0.98 mol) over a 1 hr period at 45° C.–50° C., heated at 55° C.–60° C. for 1.5 hr and poured into 328 g of 14% HCl with cooling. The resultant mixture is separated. The title product is obtained as a 32% solution in the organic phase, identified by HRGC analysis, total yield is 198.2 g (87% yield).

EXAMPLE 4

Preparation of Diethyl 5-methylpyridine-2,3-dicarboxylate via Diethyl Ethoxyoxalacetate

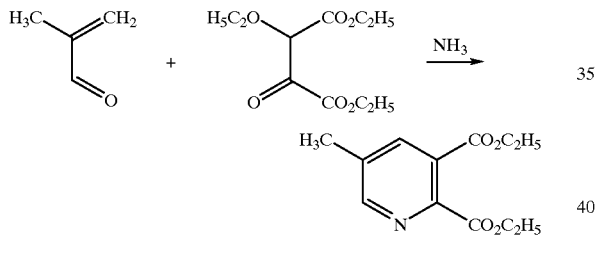

A solution of diethyl ethoxyoxalacetate (120.1 g, 82.9%, 0.43 mol) in ethanol is treated with a mixture of methacrolein (38.9 g, 97.1%, 0.54 mol) and acetic acid (42 g, 0.70 mol) at room temperature, then treated with anhydrous ammonia (9.2 g, 0.54 mol) over a 1 hr period at 25° C.–45° C., heated at reflux temperatures for 2 hr, cooled to room temperature and concentrated in vacuo to give a residue. The residue is treated with toluene, washed with 2NHCl and further concentrated in vacuo. The resultant residue is vacuum distilled to give the title product as a yellow oil, 74.06 g, 100% pure (73% yield), bp 150° C./6.5 mmHg–170° C./2.5 mmHg, identified by $^{13}$CNMR, $^{1}$HNMR.

EXAMPLE 5

Preparation of Diethyl 5-methylpyridine-2,3-dicarboxylate via the Sodium Salt of Diethyl Ethoxyoxalacetate

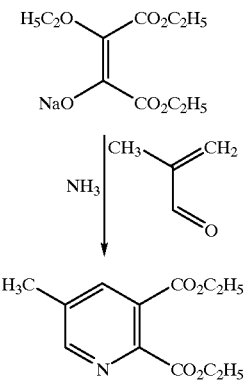

A mixture of molten sodium metal (24.15 g, 1.05 mol) in toluene is treated with ethanol (55.2 g, 1.2 mol) over a 1 hr period at 100° C.–110° C., heated at reflux temperatures for 15 minutes, cooled to room temperature, treated with diethyl oxalate (160.6 g, 1.1 mol) at 24° C.–45° C., then treated with ethyl ethoxyacetate (132 g, 98%, 0.98 mol) over an 0.5 hr period at 45° C.–50° C., and heated at 50° C.–55° C. for 2 hr to give a homogeneous solution. One half of this homogeneous solution is treated with acetic acid (75 g, 1.25 mol) at 25° C.–40° C., then treated with methacrolein (38.4 g, 91.4%, 0.50 mol), further treated with anhydrous ammonia (11 g, 0.65 mol) over a 0.5 hr period at 40° C.–60° C., heated at reflux for 2 hr, cooled to room temperature and treated sequentially with water and concentrated HCl (65 g). The resultant mixture is separated to give the title product as a 20.4% solution in the organic phase, 88.6 g (76% yield), identified by HPLC analysis.

EXAMPLE 6

Preparation of Dimethyl 5-methylpyridine-2,3-dicarboxylate via the Sodium Salt of Dimethyl Methoxyoxalacetate

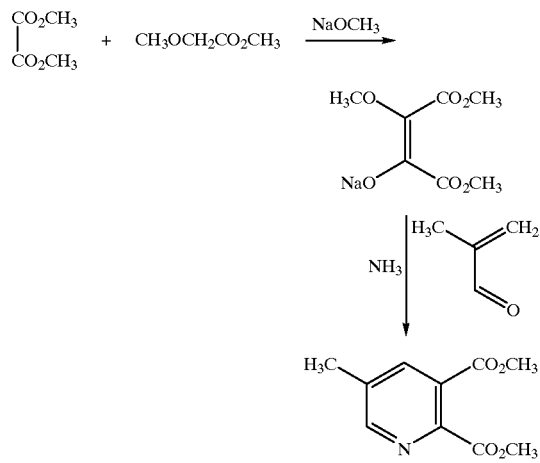

A mixture of 25% methanolic sodium methoxide (237.6 g, 1.1 mol NaOCH$_3$) and toluene is treated with a mixture of dimethyl oxalate (129.8 g, 1.1 mol) and methyl methoxyacetate (104 g, 1 mol) at 40° C.–45° C. over a 1 hr period, heated at 45° C.–50° C. for 2 hr, treated sequentially with acetic acid (150 g, 2.5 mol) and methacrolein (93 g, 95%, 1.26 mol) treated with anhydrous ammonia (18.2 g, 1.07 mol) over a 1 hr period at 40° C.–60° C., heated at reflux for 2 hr, cooled to room temperature and diluted with water. The phases are separated and the aqueous phase is extracted with toluene. The organic phase and toluene extracts are combined and concentrated in vacuo to give the title product as a 45.8% toluene solution, 91.6 g (44% yield) identified by HPLC analysis.

Using essentially the same procedure described hereinabove and substituting methyl methylthioacetate for methyl methoxyacetate the title product is obtained as a 12% solution in toluene, 54.9% yield, identified by HRGC.

EXAMPLE 7

Preparation of Dimethyl 5-methylpyridine-2,3-dicarboxylate via Methylthioacetate and an Ammonium Salt

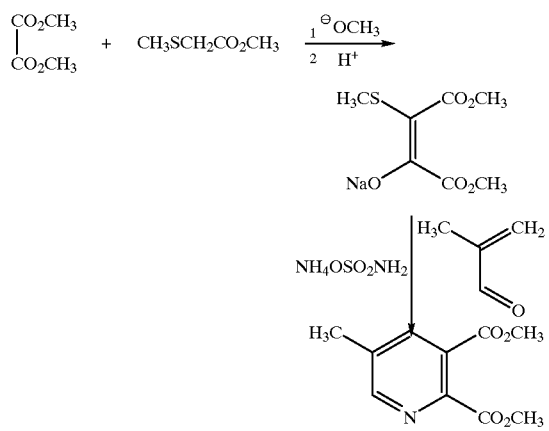

A mixture of methyl methylthioacetate (25 g, 0.21 mol) and dimethyl oxalacetate (24.6 g, 0.21 mol) in toluene is added to a slurry of sodium methoxide (12.4 g, 0.23 mol) in toluene. The resultant reaction mixture is heated at 80° C. for 5 hr, treated with additional sodium methoxide (4.5 g, 0.08 mol), further heated at 80° C. for 5 hr, cooled to room temperature and poured into dilute aqueous HCl. The mixture is separated and the aqueous phase is extracted with toluene. The organic phases are combined and concentrated in vacuo to give a residue. The residue is dissolved in methanol, treated with ammonium sulfamate (47.5 g, 0.42 mol) and methacrolein (30.7 g, 95%, 0.42 mol), heated at reflux temperatures for 20 h, and concentrated in vacuo to give a residue. This residue is partitioned between toluene and water. The aqueous phase is extracted with toluene. The organic phases are combined and concentrated to give the title product as a 4.8% toluene solution, 5.7 g product (13% yield), identified by HPLC analysis.

EXAMPLE 8

Preparation of Diethyl 5-methylpyridine-2,3-dicarboxylate via Diethyl Ethoxyoxalacetate and an Ammonium Salt

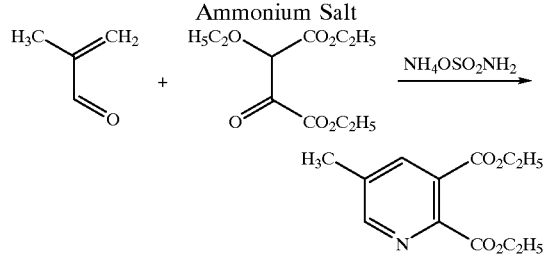

A solution of diethyl ethoxyoxalacetate (4.1 g, 96%, 17 mmol) in ethanol is treated with methacrolein (1.4 g, 95%, 19 mmol) and ammonium sulfamate (2.3 g, 20 mmol), heated at reflux temperatures for 15 hrs, cooled to room temperature and concentrated in vacuo to give a residue. The residue is dispersed in a mixture of toluene and water. The resultant mixture is separated. The aqueous phase is further extracted with toluene. The organic phases are combined and concentrated to give the title product as a 7.8% toluene solution, 2.95 g product (74% yield), identified by HPLC analysis.

EXAMPLE 9

Preparation of Diethyl 5-ethylpyridine-2,3-dicarboxylate via Diethyl Ethoxyoxalacetate and an Ammonium Salt

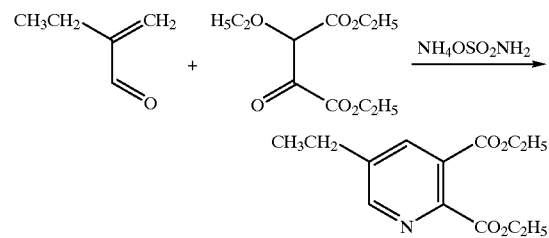

A solution of diethyl ethoxyoxalacetate (2.05 g, 96%, 8.5 mmol) in ethanol is treated with ethacrolein (0.82 g, 9.8 mmol) and ammonium sulfamate (1.16 g, 10.2 mmol) heated at reflux temperatures for 15 hr and concentrated in vacuo to give a residue. The residue is treated with a 1:1 mixture of toluene and water. The mixture is separated. The aqueous phase is extracted with toluene. The organic phases are combined and concentrated to give the title product as a 4.5% toluene solution (78% yield) by HPLC analysis.

EXAMPLE 10

Preparation of Diethyl amino ethoxymaleate (a) and Diethyl Amino Ethoxyfumarate (b)

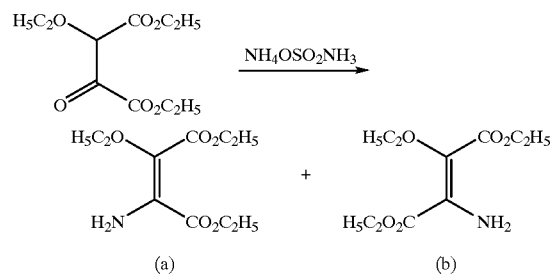

A solution of diethyl ethoxyoxalacetate (2.1 g, 96%, 8.7 mmol) in ethanol is treated with ammonium sulfamate (1.2 g, 10.5 mmol), heated at reflux temperatures until reaction is complete by GC analysis (7 hr) and concentrated in vacuo to give a residue. The residue is partitioned between methylene chloride and water. The aqueous phase is extracted with methylene chloride. The organic phases are combined, dried over $Na_2SO_4$ and concentrated in vacuo to give the title products as a yellow oil, 1.93 g (92% yield), identified by $^1$HNMR, $^{13}$CNMR, mass spectral and HRGC analyses to be a 1:1.5 mixture of a:b.

EXAMPLE 11

Preparation of Diethyl 5-methylpyridine-2,3-dicarboxylate via Diethyl Amino Ethoxymaleate and Diethyl Amino Ethoxyfumarate

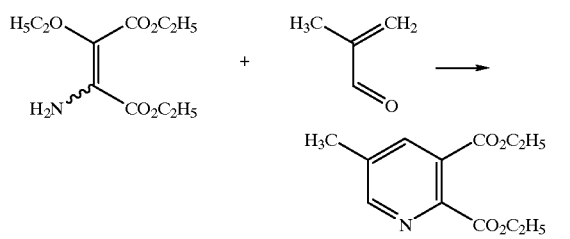

A mixture of diethyl amino ethoxymaleate and diethyl amino ethoxyfumarate (1.93 g, 8.3 mmol) in ethanol is treated with methacrolein (0.7 g, 95%, 9.5 mmol) heated at reflux temperatures for 15 hr and concentrated in vacuo to give a residue. The residue is partitioned between toluene and water. The phases are separated and the aqueous phase is extracted with toluene. The organic phases are combined and concentrated to give the title product as a 7.1% toluene solution.

EXAMPLE 12

Preparation of Dialkyl 5-alkylpyridine-2,3-dicarboxylates via Dialkyl Alkoxyoxalacetate

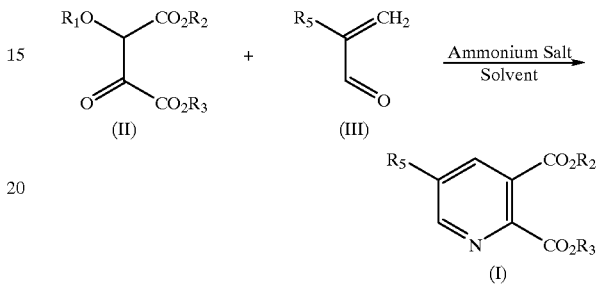

Using essentially the same procedures described in the examples set forth hereinabove, the following 5-alkyl-pyridine diester products are obtained and characterized by HPLC analyses. The reaction conditions and product yields are shown below in Table I.

TABLE I

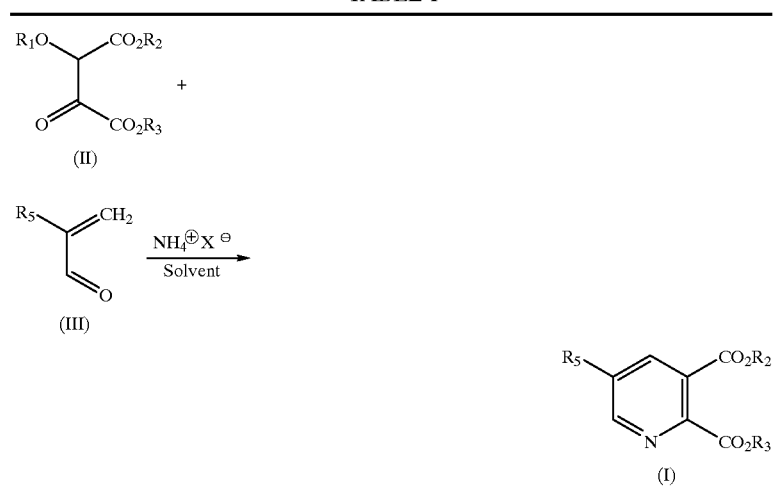

| $R_1$ | $R_5$ | $R_2$ | $R_3$ | Ratio II:III | Equiv. $NH_4^{\oplus} X^{\ominus}$ | Solvent | Temp °C. | Rxn Time (h) | (I) % Yield |
|---|---|---|---|---|---|---|---|---|---|
| $C_2H_5$ | $CH_3$ | $C_2H_5$ | $C_2H_5$ | 1:1.3 | 1.2 $CH_3CO_2^{\ominus}$ | Toluene | Reflux | 12 | 70 |
| $C_2H_5$ | $CH_3$ | $C_2H_5$ | $C_2H_5$ | 1:1.2 | 1.2 $CH_3CO_2^{\ominus}$ | Ethanol | Reflux | 6 | 86 |
| $C_2H_5$ | $CH_3$ | $C_2H_5$ | $C_2H_5$ | 1:1.4 | 1.2 $CH_3CO_2^{\ominus}$ | Ethanol | Reflux | 4 | 100 |
| $C_2H_5$ | $CH_3$ | $C_2H_5$ | $C_2H_5$ | 1:1.2 | 1.2 $NH_2SO_3^{\ominus}$ | Ethanol | 120 | 3 | 85 |
| $C_2H_5$ | $CH_3$ | $C_2H_5$ | $C_2H_5$ | 1:1.3 | 1.1 $NH_2SO_3^{\ominus}$ | Ethanol | 120 | 5 | 83 |
| $CH_3$ | $CH_3$ | $CH_3$ | $CH_3$ | 1:1.5 | 1.2 $CH_3CO_2^{\ominus}$ | Methanol | Reflux | 7.5 | 62 |
| $CH_3$ | $CH_3$ | $CH_3$ | $CH_3$ | 1:1.5 | 1.5 $NH_2SO_3^{\ominus}$ | Methanol | Reflux | 6 | 48 |
| $C_2H_5$ | $CH_3$ | $C_2H_5$ | $C_2H_5$ | 1:1.5 | 1.2 $HCO_3^{\ominus}$ | Ethanol | Reflux | 6 | 69 |
| $C_6H_5$ | $CH_3$ | $CH_3$ | $CH_3$ | 1:1.2 | 1.2 $CH_3CO_2^{\ominus}$ | Methanol | Reflux | 10 | 82 |
| $C_2H_5$ | $CH_3$ | $C_2H_5$ | $C_2H_5$ | 1:1.5 | 1.2 $CH_3CO_2^{\ominus}$ | Mixture[1] | Reflux | 6 | 89 |

[1]20% Ethanol in toluene

I claim:

1. A process for the manufacture of a compound of formula V

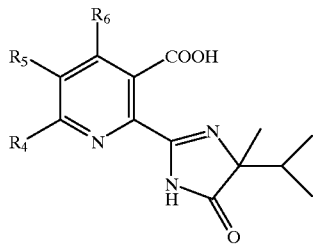
(V)

wherein $R_4$ and $R_6$ are each independently H, $C_1$–$C_6$alkyl, $C_1$–$C_6$alkenyl, phenyl or substituted phenyl; and $R_5$ is H; halogen; $C_1$–$C_6$alkyl optionally substituted with one or more $C_1$–$C_4$alkoxy groups; $C_1$–$C_6$alkenyl; phenyl or substituted phenyl which comprises:

reacting a compound of formula II or the alkali metal salt thereof

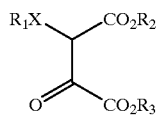
(II)

wherein X is O or S; $R_1$ is $C_1$–$C_6$alkyl, phenyl or substituted phenyl; and $R_2$ and $R_3$ are each independently $C_1$–$C_6$alkyl, phenyl or substituted phenyl with at least one molar equivalent of a compound of formula III

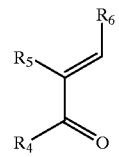
(III)

wherein $R_4$, $R_5$ and $R_6$ are as described for formula V and an ammonia source in the presence of a solvent optionally at an elevated temperature to give a compound of formula I

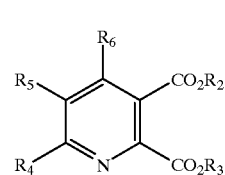
(I)

wherein $R_2$, $R_3$, $R_4$, $R_5$ and $R_6$ are described hereinabove; reacting said formula I compound with an amino amide of formula VI

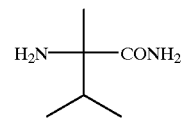
(VI)

in the presence of an inert solvent and a strong base to give the carboxylate salt of the desired formula V compound;

and acidifying said carboxylate salt to give the desired free carboxylic acid compound of formula V.

* * * * *